United States Patent [19]

Robinson

[11] Patent Number: 4,892,554
[45] Date of Patent: Jan. 9, 1990

[54] PROSTHETIC FOOT

[76] Inventor: David L. Robinson, 37 Ferrin Pl., Mt. Clemens, Mich. 48043

[21] Appl. No.: 135,588

[22] Filed: Dec. 21, 1987

[51] Int. Cl.⁴ .............................................. A61F 2/66
[52] U.S. Cl. ...................................................... 623/55
[58] Field of Search ...................................... 623/47-56

[56]  References Cited

U.S. PATENT DOCUMENTS

| | | |
|---|---|---|
| 78,048 | 5/1868 | Briody . |
| 1,289,580 | 12/1918 | Vincenti ................ 623/54 |
| 1,767,868 | 6/1930 | Barghausen . |
| 1,951,622 | 3/1934 | McElroy . |
| 2,475,372 | 7/1949 | Catranis ................ 623/54 |
| 2,475,373 | 7/1949 | Catranis . |
| 2,640,200 | 6/1953 | Wisbrun . |
| 2,644,165 | 7/1953 | Grisoni . |
| 2,731,645 | 1/1956 | Woodall . |
| 3,480,972 | 12/1969 | Prahl ..................... 623/50 |
| 3,551,914 | 1/1971 | Woodall . |
| 4,007,497 | 2/1977 | Haupt .................... 623/55 |
| 4,605,417 | 8/1986 | Fleischauer ............ 623/49 |
| 4,652,266 | 3/1987 | Truesdell ............... 623/55 |

FOREIGN PATENT DOCUMENTS 41802  2/1918  Fed. Rep. of Germany ........ 623/55

Primary Examiner—Richard J. Apley
Assistant Examiner—James Prizant
Attorney, Agent, or Firm—Steven L. Permut

[57] ABSTRACT

A prosthetic foot includes an ankle member, a heel member and an elongate metatarsal-toe member coupled to each other for relative pivotal movement resisted by resilient pads engaged between the respective members. The undersides of the heel and toe members are concavely arched, the length of the arch duplicating that of a natural foot of the same size, with the center of the arch vertically aligned with the center of gravity of the amputee when in a standing, foot-flat position. The toe member is partially bifurcated at its forward end to provide independently flexible toe sections at the inner and outer sides of the foot, achieving a stable, three-point support matching that of a natural foot.

9 Claims, 2 Drawing Sheets

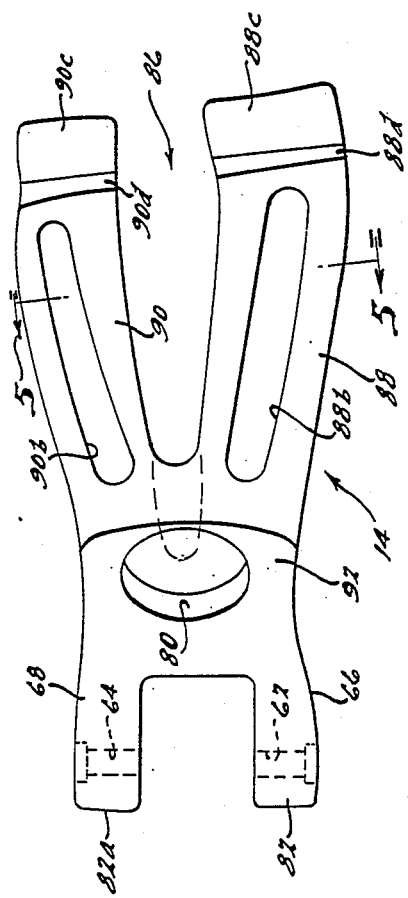
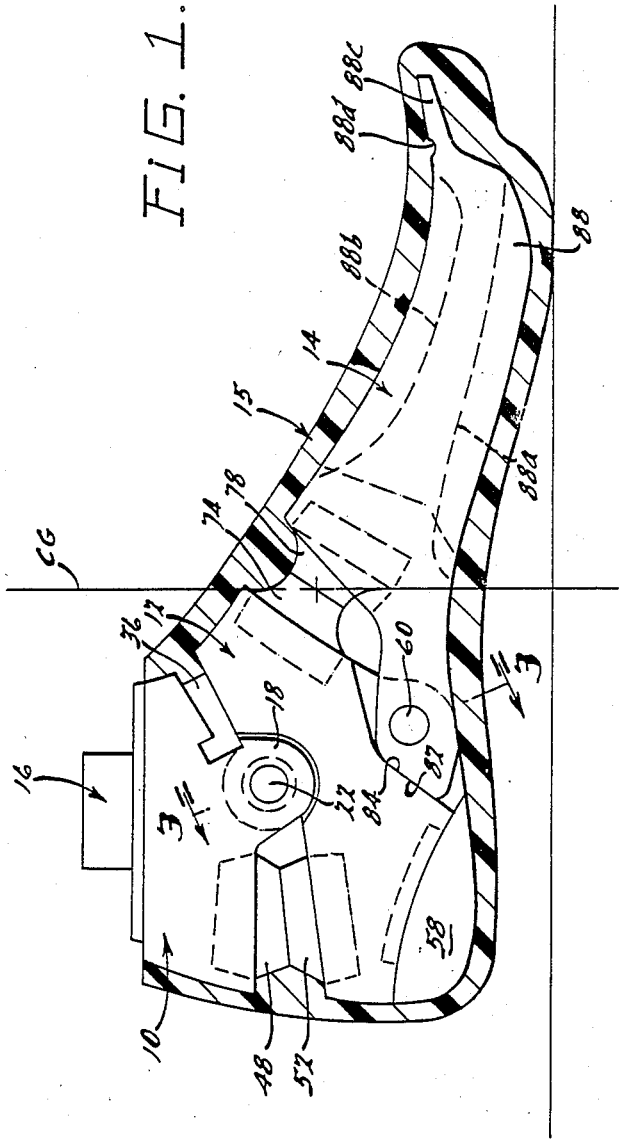

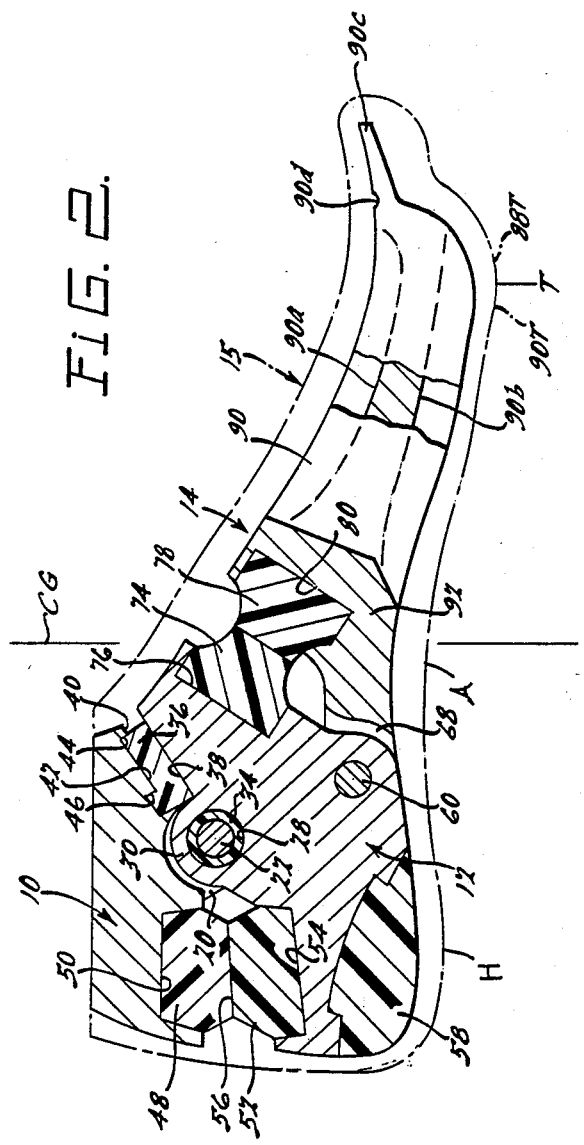

PROSTHETIC FOOT

BACKGROUND OF THE INVENTION

The human foot presents a complex skeletal structure having numerous joints which are in turn controlled by a complex muscular system. While reasonably close mechanical equivalents of the skeletal structure of the foot might be constructed without any great difficulty, the provision of a control system capable of manipulating such a mechanical system to duplicate the action of a human foot presents a far greater problem both from the technological and the financial standpoints.

As a result, presently available prosthetic feet typically take the form of two or more elements coupled to each other for resiliently resisted, pivotal or flexing movement relative to each other in movement approximately duplicative of the flexing movement of portions of the human foot. Many examples of such prosthetic feet exist in the prior art; however, as noted in Truesdell Pat. No. 4,652,266, very few have met with complete approval from amputees and prosthetic specialists.

The basic requirements of an acceptable prosthetic foot are that it will provide a stable support for the amputee throughout a reasonable range of activity and permit the amputee to walk with a normal stride. To achieve this normal stride, the prosthetic foot must flex during walking as the foot continually moves through the heel-strike, foot-flat and toe-off cycle. It must also, throughout this cycle, provide transverse stability, particularly at toe-off, when the entire weight of the amputee is applied to the forward portion of the prosthetic foot. Prior art prosthetic feet typically are substantially transversely inflexible, which interferes with side-to-side balancing when walking on uneven surfaces. Unlike the natural foot, the prosthetic foot does not sense or correct itself for this unevenness and an unanticipated sidewise tilting of the foot at toe-off results in an imbalance at a critical portion of the stride.

In the case of a unilateral (one-legged) amputee, it is not possible to match the stride of the prosthetic foot with that of the natural foot unless the weight transfer from the points of support of the foot duplicate each other in the prosthetic foot and the natural foot. This requirement has not been fully appreciated by the prior art, particularly in duplicating the geometrical relationship between the amputee's center of gravity and points of support throughout heel-strike, foot-flat and toe-off. Unless, for example, the heel-strike of the prosthetic foot occurs at the same point in the stride cycle as that of the natural foot, the gait will be uneven. Similarly unless the transition of weight to the forward portion of the prosthetic foot—initiation of toe-off—does not match that of the natural foot, a hitch in stride or lurch will occur.

The present invention is directed to a prosthetic foot which presents a three-point balance system matching that of a natural foot.

SUMMARY OF THE INVENTION

In accordance with the present invention, a prosthetic foot is made up of three major components cooperatively conformed in overall shape to roughly approximate a human foot. The three major elements include an upper or ankle member, a heel member underlying and pivotally connected to the ankle member for pivotal movement about a first transverse axis, and an elongate metatarsal-toe member whose rearward portion underlies the forward portion of the heel member and which is pivotally connected at its rearward end to the heel member for pivotal movement about a second transverse axis. The under portions of the heel and toe members are shaped in a longitudinally extending concave arch so that, when rested upon a flat surface, the bottom of the foot engages the flat surface at a support point on the heel member at the rearward end of the arch and at points on the underside of the toe member at the forward end of the longitudinal arch. The toe member is formed with a reasonably wide, longitudinal slot which extends rearwardly from the forward end of the toe member for approximately one-half the length of the toe member so that the forward end of the toe member is bifurcated with elongate toe sections at the inside and outside of the foot extending forwardly from a main body portion of the toe member in cantilevered relationship to the body portion. The ankle, heel and toe members of the foot are preferably molded from a suitable thermoplastic material, such as nylon, and the bifurcated toe sections at the forward end of the toe member may be grooved or otherwise configured in a manner such that they are capable of independent flexing movement to some extent relative to the main body portion of the toe member. At the forward end of the toe section, the support points on the bottom of the foot which will rest upon a flat surface are located at opposite sides of the longitudinal slot, one point on each of the two toe sections. This, in cooperation with the heel support points, provides a stable, three-point support for the foot when in the foot-flat position.

The first pivotal axis which couples the ankle and heel members of the prosthetic foot is at a location slightly below that of the ankle joint of a human foot. To the rear of this axis, the underside of the ankle member and the upper side of the heel member are provided with resilient pads having opposed, engaged flat surfaces which are disposed in an approximately horizontal position. At the forward side of the first axis, a resilient pad on the underside of the ankle member engages a flat surface on the opposed upper portion of the heel member, this surface being forwardly and upwardly inclined at an angle somewhat less than 45 degrees to the horizontal. This latter pad is substantially less compressible than the opposed pads at the rear of the first axis. The pads are so dimensioned that all three pads are slightly compressed under normal circumstances to maintain the ankle and heel members at a pivotal rest position with respect to the first axis. The pivot assembly which defines the first axis includes a pin seated at its opposite ends in downward projections at opposite sides of the ankle member and having an elongate central portion received within a bushing mounted in the heel member. The bushing is formed of a material which possesses a sufficient degree of resilience to enable a slight rocking of the heel member relative to the ankle member about axes normal to that of the pivot pin.

The pivot which connects the heel member to the toe member is a simple pivot defined by a rigid pin passing through aligned bores in the heel and toe members so that the second pivot axis is fixed relative to the heel member. Rearwardly of the second pivot axis, a resilient pad is fixedly mounted on the underside of the heel to define a heel pad which cushions the heel-strike portion of the stride. At a location above and forwardly of the second axis, resilient pads are mounted respectively in opposed portions of the heel and toe members to engage each other at opposed flat surfaces which lie in a plane inclined upwardly and forwardly of the foot at an angle somewhat greater than 45 degrees from the horizontal. Abutment surfaces engageable between the toe member and heel member limit downward pivotal movement of the forward end of the toe member relative to the heel member to dispose these members normally in a position comparable to that of an unweighted human foot. The pads engaged between the toe member and heel member are so dimensioned that when the foot is unweighted, the abutment surfaces on the heel and toe members are engaged with a slight loading; that is, the pads on the heel and toe members are slightly compressed. The compression characteristics of the pads between the heel and toe members are similar to that of the pad engaged between those portions of the ankle and heel members forwardly of the first axis.

The configuration of the foot embodying the present invention is such that a sagittal plane passing through the center of gravity of an amputee using the foot will pass through the inclined, engaged faces of the pads between the heel and toe members, and pass downwardly through the center of the longitudinal arch of the foot, i.e. midway between the support points on the bottom of the heel and toe sections when the foot is in a foot-flat position.

Other objects and features of the invention will become apparent by reference to the following specifications and to the drawings.

BRIEF DESCRIPTION OF THE DRAWINGS

FIG. 1 is a side elevational view of a prosthetic foot embodying the present invention with an outer layer of material cut away and shown in section;

FIG. 2 is a cross-sectional view of the foot taken on a vertical plane passing longitudinally centrally through the foot, with a portion of the toe section broken away;

FIG. 3 is a detailed cross-sectional view taken on the line 3—3 of FIG. 1;

FIG. 4 is a top plan view of the toe member of the foot; and

FIG. 5 is a detailed cross-sectional view taken on the line 5—5 of FIG. 4.

DESCRIPTION OF THE PREFERRED EMBODIMENT

Referring first particularly to FIGS. 1 and 2, a prosthetic foot embodying the present invention includes what will be referred to as an ankle member designated generally 10, a heel member designated generally 12 and a toe member designated generally 14. Members 10, 12 and 14 are preferably molded of a suitable, relatively hard thermoplastic material, such as nylon or a suitable polyurethane. When assembled, members 10, 12 and 14 are enclosed within an outer layer 15 of a reasonably firm, resilient, elastomeric material whose outer surface is conformed to that of a natural foot. A suitable attachment member schematically illustrated at 16 is fixedly secured to the upper side of heel member 10 to enable the foot to be attached to the stump or a section of an artificial leg of the amputee. Several well-known forms of such attachments are commercially available, such as the Otto Bock endo-skeletal and exo-skeletal systems. For present purposes, it is sufficient to note that attachment 16 is intended to fixedly attach ankle member 10 to the lower end of an artificial leg or stump.

As best seen in FIGS. 1 and 3, at opposite sides of ankle member 10, integral, downwardly projecting ears 18, 20 are formed. A rigid pivot pin 22, FIG. 3, is received at its opposite ends within coaxially aligned bores 24, 26 in ears 18, 20 and also passes through a bore 28 in an upward projection 30 integrally formed on heel member 12 which projects upwardly with some clearance into the recess between ears 18 and 20. As best seen in FIG. 3, the opposite ends of bore 28 through heel member 12 are formed with inwardly tapered counterbores 32, and a bushing 34 of a material possessing some resilience coaxially receives pivot pin 22 within bore 28. The frusto-conical enlargements or thickened sections at the ends of bushing 34 accommodate some flexing movement of heel member 12 relative to ankle member 10 about axes other than the axis of pin 22 to permit a limited degree of sidewise tilting (about an axis extending longitudinally of the foot) or twisting (a vertical axis) of heel member 12 relative to ankle member 10.

Referring now particularly to FIG. 2, a first resilient pad 36 is engaged between opposed surfaces 38 and 40 on heel member 12 and ankle member 10 at a location forwardly of pivot pin 22. Pad 36 is retained within a recess 42 in surface 40 of ankle member 10, as by a suitable adhesive, and recess 42 is formed with shoulders as at 44 and 46 to prevent extrusion of pad 36 outwardly from between the heel and ankle members upon compression. The lowermost surface of pad 36 rests upon surface 38 of heel member 12, but is not attached to this latter surface.

At a location rearwardly of pivot pin 22, a second resilient pad 48 is retained within a downwardly opening recess 50 in the lower surface of ankle member 10 and engages a generally similar pad 52 seated within an upwardly opening recess 54 in the upper surface of heel member 12. The interengaged faces 56 of pads 48 and 52 lie in a generally horizontal plane extending radially of pivot pin 22.

Pads 36, 48 and 52 are preferably formed of a suitable urethane or other rubber-like material, with pad 38 being substantially harder, i.e. less compressible, than pads 48 and 52. The pads are so dimensioned as to be slightly compressed when heel member 12 and ankle member 10 are in the normal rest relationship shown in FIG. 2; in other words, the opposed pivotal biasing action of the pads is counterbalanced when the heel and ankle members are in a normal rest position relative to one another. The compressive characteristics of pad 36 are such that clockwise pivotal movement of ankle member 10 about the axis of pivot pin 22 is limited to an amount such that separation between the rear pads 48, 52 cannot occur. However, rear pads 48 and 52 are sufficiently resilient to accommodate counterclockwise pivotal movement of ankle member 10 about the axis of pin 22 to an extent such that pad 36 can be separated from surface 38 of heel member 12. When heel member 12 is in its normal relationship to ankle member 10 as shown in FIG. 2, surface 38 of heel member 12 extends generally radially from the axis of pin 22 and is inclined upwardly and forwardly at an angle somewhat less than 45 degrees from the horizontal.

A resilient heel pad is fixedly secured to the lower rear portion of heel member 12. Heel pad 58 functions primarily as a cushioning pad which cushions the impact at heel-strike during walking. Pad 58 is fixedly secured, as by any suitable means, in the position shown in FIG. 2 upon heel member 12.

As best seen in FIG. 3, a rigid pivot pin 60 is passed through aligned bores 62 and 64 of spaced, opposed, rearward projections 66 and 68 integrally formed on toe member 14 and through an aligned bore 70 in a downward projection 72 integrally formed on the underside of heel member 12 to pivotally couple the heel member and toe member to each other. Unlike the pivotal connection between heel member 12 and ankle member 10, the pivotal connection provided between heel member 12 and toe member 14 is designed to restrict relative movement between the heel and toe members to pivotal movement about the axis of pivot pin 60.

At a location spaced forwardly and above pivot pin 60, a resilient pad 74 is retained within a recess 76 which faces forwardly and somewhat downwardly from heel member 12. Pad 74 is engaged in face-to-face abutment with a similar pad 78 retained within a recess 80 in toe member 14. Referring now to FIG. 1, it is seen that at the rearward end of rearward projection 66 of toe member 14, an inclined, flat surface 82 on projection 66 engages a complementarily inclined abutment surface 84 on heel member 12. The engagement between these two surfaces 82 and 84 defines a positive end limit of clockwise pivotal movement of toe member 14 relative to heel member 12 as viewed in FIG. 1, and the dimensions and resilient characteristics of pads 74 and 78 are such that surfaces 82 and 84 are normally resiliently biased into the engagement illustrated in FIG. 1. The other rearward projection 68 of toe member 14 is formed with a similar abutment surface 82a (FIG. 4) which engages a corresponding abutment surface on heel member 12.

Referring now to FIG. 4, which is a top plan view of a toe member 14 of a left foot, it is seen that a longitudinally extending slot 86 extends rearwardly from the front of toe member 14 for a substantial distance (approximately one-half of the length of toe member 14) to divide the forward portion of the toe member into inner 88 and outer 90 toe sections. Toe member 14 is formed as a monolithic or one-piece member of a thermoplastic material, such as nylon, which is reasonably hard but possesses sufficient elasticity so that the elongate, cantilevered toe sections 88, 90 are capable of some flexing movement relative to the main body section 92 of toe member 14 to which they are integrally joined at their rearward ends. The flexing characteristics of toe sections 88 and 90 are established by the configuration of the sections, most conveniently by forming grooves 88a, 88b, 90a and 90b (see FIG. 5) of widths, depths and lengths which will result in the desired flexing action. At the forward end of each toe section, as best seen in FIGS. 1 and 2, a relatively thin tip section 88c, 90c projects forwardly from the top of the respective toe sections 88, 90, with a lateral groove 88d, 90d being formed in the top of the respective toe sections at the juncture of the tip portions 88c, 90c with the main portion of the toe sections 88, 90. The grooves 88d, 90d provide a so-called living hinge which enables the tip sections 88c, 90c to swing upwardly relative to the remainder of the toe section at toe-off in duplication of the flexing of the toes of a natural foot at toe-off.

The constructional features of toe member 14 described above provide several advantages. For obvious reasons, the overall size of the prosthetic foot, in the case of a unilateral (one-legged) amputee is matched to that of the remaining natural foot. However, the size of a person's foot is not determinative of his weight or other body measurements and a heavier person, for example, will require a prosthetic foot having stiffer flexibility than would be acceptable to a person of lesser weight. The construction described above enables all toe sections 14 of feet of a given size to be uniformly formed in a molding operation and to then have the flexibility of the toe section increased by cutting additional material, as from the various grooves as may be appropriate.

The bifurcated inner and outer toe sections 88, 90 are capable of independent flexing relative to the main body portion 92; thus if one of the toe sections should bear upon a small protuberance or pebble, that toe section may flex upwardly to absorb at least a portion of this unbalancing action to minimize tilting of the entire foot. The bifurcated toe portions provide two laterally spaced support points at the front portion of the foot in the foot-flat and toe-off stages and, in the foot-flat position, cooperate with the support point under heel member 12 to provide a stable three-point support.

The bifurcated toe section of the toe member 14 achieves this foot-flat, three-point support in a manner best seen in FIG. 2. As shown in FIG. 2, when the prosthetic foot is in a foot-flat position, the undersides of heel member 12 and toe member 14 are formed to constitute an upwardly concave arch A whose forward end terminates at the region T and whose rearward end terminates at the region H. The regions H and T are the ground engaging regions or weight support points of the foot when in its foot-flat position. The forward support points at the region T are on the underside of each of toe sections 88, 90 and, as best seen in FIG. 5 where these points are respectively designated as 88T and 90T, are laterally spaced from each other and lie on the opposite sides of longitudinal slot 86. The points 88T and 90T lie on a line lying in the plane of section line 5—5 which, as best seen in FIG. 5, is inclined rearwardly and outwardly of the longitudinal centerline of the foot. The support points at 88T lie approximately in a position corresponding to the ball of a natural foot, and the inclination of the section line 5—5 relative to the longitudinal centerline of the foot corresponds to the similar line of weight engagement in a natural foot. Lateral stability of the prosthetic foot is achieved by the lateral spacing of the points 88T and 90T (FIG. 5).

Fore-and-aft stability of the foot when the amputee is standing in a stationary foot-flat position requires that the frontal plane which passes vertically through the amputee's center of gravity should pass vertically between the front and rear support points of the foot, H and T, and that optimum condition of stability will exist when the plane of this center of gravity, indicated at CG in FIGS. 1 and 2, is equidistant, longitudinally, from points H and T—i.e. through the center of arch A. As best seen in FIG. 2, the center of gravity plane CG passes well forward of pivot pins 22 and 60 and approximately vertically bisects the engaged surfaces of pads 74 and 78. With this relationship, when the amputee is standing erect in the foot-flat position, 50% of the body weight applied to the prosthetic foot of the present invention is applied at the heel support point H, while the remainder of the applied body weight is supported cooperatively by the forward support points 88T and 90T. As stated above, the preloading compression between pads 74 and 78 which biases the abutment surfaces 82, 84 (FIG. 1) on the heel and toe members into engagement with each other is adjusted to be such as to just maintain the surfaces 82, 84 in contact in the face of the applied body weight. With the amputee standing erect in a stationary position, the weight support points H and T of the prosthetic foot geometrically match and are symmetrical to the weight support points of the natural foot.

Because of the matching of the relationship of the support points of the prosthetic foot to the center of gravity of the amputee with those of the natural foot, the engagement of the prosthetic foot with the ground during walking will also match that of the normal foot. The angulation of the leg carrying the prosthetic foot at heel-strike will match that of the opposite natural foot; and since the length of the arch of the prosthetic foot matches that of the natural foot, the heel-strike of the prosthetic foot will take place at the corresponding location of heel-strike of the natural foot. This is extremely important because otherwise an unevenness in gait-limping will occur. Like a natural foot, the force produced at heel-strike will, in the prosthetic foot of the present invention, cause the forward portion of the prosthetic foot to swing downwardly to minimize the interval between heel-strike and foot-flat positioning. In the present prosthetic foot, upon heel-strike, heel member 12 is pivoted in a clockwise direction as viewed in FIGS. 1 and 2 about pivot 22, this pivotal action being resisted by the relatively soft opposed pads 48, 52 at the rear of pivot 22. This clockwise pivotal action of heel member 12 is directly transmitted to toe member 14, the heel and toe members being maintained in the angular relationship shown in FIGS. 1 and 2 by the preloaded compression of pads 74 and 78 which maintain the abutment surfaces 82 and 84 between the heel and toe members in contact with each other.

As the stride progresses to and through the foot-flat position, the ankle and heel members 10 and 12 return to the relationship shown in FIGS. 1 and 2; and as the center of gravity moves forward as the stride continues, the proportion of the weight supported at the forward support points T of the prosthetic foot progressively increases. This progressive increase exerts a pivotal biasing action tending to pivot toe member 14 in a counterclockwise direction about pivot 60. This pivotal force is transmitted via pads 78, 74 to heel member 12 and is, at this stage in the stride, directly opposed by the forces developed by the forwardly shifted center of gravity upon ankle member 10. The pad 36 engaged between ankle member 10 and heel member 12 is extremely firm, and substantially no pivotal movement between the ankle and heel members occurs as the foot moves from the foot-flat portion to the toe-off portion of the stride cycle. Flexing of toe member 14 relative to the now substantially rigid heel and ankle members is resisted by pads 74, 78. The rate at which this resistive force between pads 74 and 78 increases is determined by the compressibility or hardness of the material of these pads and can be also influenced by the cross-sectional configuration of the pads. As this compressive force increases, eventually forces sufficient to cause flexing of the bifurcated toe sections will occur; and as the toe-off point is approached, tip sections 88c and 90c will eventually begin to bear weight and flex accordingly. In the final portions of the toe-off stage of the stride, with all of the weight supported upon toe member 14, tip sections 88c 90c assist the bottom or ball portion of the prosthetic foot in supporting the weight, and spread this support over a greater area to provide greater stability at toe-off.

While one embodiment of the invention has been described in detail, it will be apparent to those skilled in the art that the disclosed embodiment may be modified. Therefore, the foregoing description is to be considered exemplary rather than limiting, and the true scope of the invention is that defined in the following claims.

What is claimed is:

1. A prosthetic foot comprising an ankle member, a heel member underlying said ankle member, first pivot means coupling said heel member to said ankle member for resiliently resisted pivotal movement about a first transverse axis, an elongate metatarsal-toe member having a rear portion underlying a forward portion of said heel member and projecting forwardly from said heel member, second pivot means coupling said toe member to said heel member for pivotal movement about a second transverse axis, positive stop means engageable between said heel and toe members define an end limit to downward pivotal movement of the forward end of said toe member relative to said heel member, compression means engaged between said heel and toe members for resiliently resisting upward pivotal movement of the forward end of said toe member relative to said heel member, said toe member having an elongate slot therethrough extending longitudinally rearwardly from the forward end of said toe member bifurcating the forward portion of said toe member, the underside of said heel and toe members being conformed to cooperatively define a longitudinally extending concave arch, first means on said heel member defining a weight supporting support point on the underside of said heel member at the rearward end of said arch, second means on said toe member defining first and second weight supporting support points on the underside of said toe member at the forward end of said arch respectively located at opposite sides of said slot, said support points defining a stable three-point support for said foot when in a foot-flat position, and said first and second axes being spaced rearwardly from the center of said arch.

2. The invention as defined in claim 1 wherein the center of gravity of an amputee using said foot is in approximate vertical alignment with said mathematical center of said arch when the amputee is in a normal standing position.

3. The invention defined in claim 2 wherein said compression means is operable to maintain said positive stop means engaged when the amputee is in a normal standing position.

4. The invention defined in claim 1 wherein said first pivot means comprises first compressible resilient means engaged between said heel and ankle members rearwardly of said first axis and second compressible resilient means engaged between said heel and ankle members forwardly of said first axis, said first resilient means having a greater degree of resilience than said second resilient means.

5. The invention defined in claim 1 wherein said first pivot means comprises an elongate rigid pivot pin received within axially spaced bores in one of said ankle and heel members and received within an axially elongate bushing mounted in a portion of the other of said ankle and heel members axially aligned with and located between said bores, said bushing being of a resilient material accommodating limited resiliently resisted pivotal movement of said ankle and heel members relative to each other about axes other than said first axis.

6. The invention defined in claim 1 wherein said toe member is a one-piece member including a main body portion extending transversely across said toe member rearwardly of said slot, elongate inner and outer toe sections integrally joined at their rearward ends to said body portion and projecting forwardly from said body portion at opposite sides of said slot, said toe sections being capable of limited independent flexing movement in a vertical plane relative to said main body.

7. The invention defined in claim 6 wherein each of said toe sections terminates at its forward end in a relatively thin tip section projecting generally horizontally forwardly from the top of said toe section.

8. A prosthetic foot comprising an ankle member, a heel member underlying said ankle member, a first pivot means coupling said heel member to said ankle member for resiliently resisted pivotal movement about a first transverse axis, an elongated metatarsal toe member having a rear portion underlying a forward portion of said heel member and projecting forwardly from said heel member, said toe member pivotably connected about a second transverse axis to said heel member, said heel member having a portion interposed between said ankle member and said toe member, compression means engaged between said heel portion and toe member for resiliently resisting upward pivotal movement of the forward end of said toe member relative to said heel member, a resilient means between said heel portion and said ankle member for resisting upward motion of said heel portion relative to said ankle member; resilient compressible means for resisting downward movement of said heel portion relative to said ankle member with the resilient compressible means having a greater degree of compressibility than said resilient means;

a positive stop means engageable between said heel and toe members defining an end limit to downward pivotal movement of the forward end of said toe member relative to said heel member;

the underside of said heel and toe members being conformed to cooperatively define a longitudinally extending concave arch, said first and second transverse axes being spaced rearwardly from the center of said arch;

first and second weight supporting points on the underside of said toe member at the forward end of said arch respectively laterally displaced from each other;

means for changing the relative vertical position of said first and second weight supporting points.

9. A prosthetic foot comprising an ankle member, a heel member underlying said ankle member, first pivot means coupling said heel member to said ankle member for resiliently resisted pivotal movement about a first transverse axis, an elongate metatarsal toe member having a rear portion underlying a forward portion of said heel member and projecting forwardly from said heel member, second pivot means coupling said toe member to said heel member for pivotal movement about a second transverse axis, positive stop means engageable between said heel and toe member define an end limit to downward pivotal movement of the forward end of said toe member relative to said heel member, compression means engaged between said heel and toe members for resiliently resisting upward pivotal movement of the forward end of said toe member relative to said heel member, said toe member extending longitudinally rearwardly from the forward end of the underside of said heel and toe members being conformed to cooperatively define a longitudinally extending concave arch, first means on said heel member defining a weight supporting support point on the underside of said heel member at the rearward end of said arch, second means on said toe member defining first and second weight supporting support points on the underside of said toe member at the forward end of said arch respectively laterally displaced from each other, said support points defining a stable three point support for said foot when in a flat foot position, said first and second weight supporting support points being independently resiliently movable in a vertical fashion from said flat foot position, and said first and second axes being spaced rearwardly from the center of said arch.

* * * * *